United States Patent [19]
Kelly

[11] Patent Number: 5,955,394
[45] Date of Patent: Sep. 21, 1999

[54] RECOVERY PROCESS FOR OXIDATION CATALYST IN THE MANUFACTURE OF AROMATIC CARBOXYLIC ACIDS

[75] Inventor: Michael D. Kelly, Memphis, Tenn.

[73] Assignee: Mobile Process Technology, Co.

[21] Appl. No.: 08/904,080

[22] Filed: Jul. 31, 1997

Related U.S. Application Data

[60] Provisional application No. 60/023,671, Aug. 16, 1996.

[51] Int. Cl.[6] .............................. B01J 20/34; B01J 37/30; B01J 38/68
[52] U.S. Cl. .............................. 502/12; 502/24; 502/27; 423/49; 423/139; 562/414
[58] Field of Search .............................. 502/12, 24, 27; 423/49, 139; 562/414

[56] References Cited

U.S. PATENT DOCUMENTS

| | | | |
|---|---|---|---|
| 2,245,528 | 6/1941 | Loder | 260/524 |
| 2,833,816 | 5/1958 | Saffer et al. | 260/524 |
| 2,964,559 | 12/1960 | Burney et al. | 260/525 |
| 3,092,658 | 6/1963 | Baldwin et al. | 260/524 |
| 3,170,768 | 2/1965 | Baldwin | 23/263 |
| 3,341,470 | 9/1967 | Hensley, Jr. | 252/413 |
| 3,380,920 | 4/1968 | Cochardt | 252/62.63 |
| 3,716,626 | 2/1973 | Kniese et al. | 423/418 |
| 3,873,468 | 3/1975 | Kobinata et al. | 502/24 |
| 3,880,920 | 4/1975 | Wampfler | 260/524 R |
| 3,956,179 | 5/1976 | Sebastian et al. | 252/430 |
| 3,959,449 | 5/1976 | Shigeyasu et al. | 423/488 |
| 4,021,463 | 5/1977 | Kummer et al. | 260/429 R |
| 4,162,991 | 7/1979 | Jones | 252/413 |
| 4,202,797 | 5/1980 | Jones | 252/413 |
| 4,238,294 | 12/1980 | Takeuchi et al. | 203/72 |
| 4,258,227 | 3/1981 | Allen et al. | 585/469 |
| 4,266,084 | 5/1981 | Allen | 585/469 |
| 4,298,759 | 11/1981 | Harper et al. | 562/485 |
| 4,312,778 | 1/1982 | Harper | 252/410 |
| 4,393,264 | 7/1983 | Allen et al. | 585/469 |
| 4,459,365 | 7/1984 | Suzuki et al. | 502/24 |
| 4,490,297 | 12/1984 | Feld et al. | 260/429 R |
| 4,546,202 | 10/1985 | Edwards et al. | 562/414 |
| 4,680,098 | 7/1987 | Chang | 204/182.4 |
| 4,786,621 | 11/1988 | Holzhauer et al. | 502/28 |
| 4,786,752 | 11/1988 | Holzhauer et al. | 562/414 |
| 4,794,195 | 12/1988 | Hayashi et al. | 562/414 |
| 4,855,491 | 8/1989 | Chew et al. | 562/414 |
| 5,183,933 | 2/1993 | Harper et al. | 562/414 |
| 5,230,804 | 7/1993 | Leupold et al. | 210/651 |
| 5,463,145 | 10/1995 | Powell et al. | 568/867 |

OTHER PUBLICATIONS

Encyclopedia of Separation Technology, vol. 2, D. Ruthven, ed., pp. 1230–1231, 1241–1249 (John Wiley & Sons 1997).

Primary Examiner—Steven Bos
Assistant Examiner—Alexander G. Ghyka
Attorney, Agent, or Firm—Ray F. Cox, Jr.

[57] ABSTRACT

An improved separation process for the continuous catalytic oxidation of aromatic alkyls for the production of aromatic carboxylic acids in a liquid solvent medium, wherein the reactor product stream is withdrawn from the oxidation process, then separated to produce a product containing stream, mother liquor stream and a catalyst containing purge stream which is then passed through a filtration system and series of sorption vessels to remove the oxidation catalyst and separate the impurities from the catalyst. The solvent is then separated from the reaction by-products by conventional distillation methods. The solvent is recycled to the process while the reaction by-product residue is disposed of by incineration. The oxidation catalyst is eluted from the ion exchange columns and returned to the process.

55 Claims, 2 Drawing Sheets

RECOVERY PROCESS FOR OXIDATION CATALYST IN THE MANUFACTURE OF AROMATIC CARBOXYLIC ACIDS

This application claims benefit of Provisional Appln No. 60/023,671, filed Aug. 16, 1996.

TECHNICAL FIELD

The present invention relates to a method for removal and recovery of the oxidation catalyst used in the manufacture of aromatic carboxylic acids. More specifically, the present invention is directed to a method of selectively removing the oxidation catalyst and separating undesirable impurities from certain aromatic carboxylic acid-bearing process streams by ion exchange. The present invention also is directed to purifying the recovered catalyst in such a manner that it can be returned to the oxidation process. Furthermore, the present invention provides for the economic recovery of residual aromatic acids "fines" and for removing metal and color-forming impurities.

BACKGROUND OF THE INVENTION

Aromatic carboxylic acids are commonly manufactured by catalytically oxidizing aromatic alkyls in the liquid phase under elevated temperature and pressure conditions. U.S. Pat. Nos. 2,245,528; 2,833,816; 3,092,658 and 3,170,768, the disclosures of which are incorporated herein by reference, are illustrative of the manufacturing process. Typically, the medium within the oxidation reactor includes the aromatic alkyl, the oxidation catalyst, an oxygen-containing gas, and a solvent, typically a lower aliphatic monocarboxylic acid.

A liquid product stream from the reactor contains in addition to the aromatic carboxylic acid, the oxidation catalyst, solvent, oxidation reaction by-products, and other process impurities. The oxidation catalyst typically consists of one or more of cobalt, manganese, and hydrogen bromide.

After cooling the product stream to crystalize the product aromatic acid, the reactor product stream is passed through a separation process to remove a major portion of the product aromatic carboxylic acid. The commonly employed means of separation is by centrifugation. The mother liquor is then returned to the oxidation reactor. A small residue purge stream, which contains the oxidation catalyst, minor residual aromatic carboxylic acids, reaction by-products, solvent and process impurities, is sent to a separation process for recovery of the solvent. This separation process produces a concentrated sludge containing the oxidation catalyst, reaction by-products and process impurities.

Considerable efforts have been directed toward removing the impurities from the previously mentioned catalyst-containing purge stream using conventional separation techniques. However, all such known methods to effectively remove the impurities from the process stream are technically impractical or economically undesirable. Such methods include chemical precipitation or incineration followed by hydrometallurgical recovery of the catalyst. Known methods using ion exchange resins do not incorporate an upstream filtering scheme for removing fine product particulate matter that degrades the function of the ion exchange resins.

U.S. Pat. No. 2,964,559 discloses a process involving liquid phase oxidation for recovering heavy metal oxidation catalysts by extracting the catalyst from distillation bottoms with a solvent.

U.S. Pat. No. 3,341,470 discloses a process for the recovery of cobalt and manganese catalysts from an oxidation reaction mixture by incinerating the stream to convert the various metals to their oxides and effecting selective chemical precipitation of the contaminants with specific reagents.

U.S. Pat. No. 3,873,468 discloses aqueous extraction from still bottoms followed by carbonate precipitation.

U.S. Pat. No. 3,959,449 also discloses an aqueous extraction from still bottoms but followed by a strongly acidic cation-exchange resin, distilling the solution to recover bromine as hydrobromic acid, and recovering the heavy metal catalysts as bromides.

U.S. Pat. No. 4,162,991 discloses recovery of cobalt and bromide catalysts by absorbing the catalysts on a strongly basic anion exchange resin and desorbing cobalt and bromide ions with lower aliphatic monocarboxylic acid.

U.S. Pat. Nos. 4,546,202; 4,266,084; 4,258,227; and 4,393,264 disclose the recovery of catalysts from pyrolysis ash.

U.S. Pat. No. 4,855,491 discloses a method employing a nanofilter to pass sodium benzoate and reject Cobalt catalysts.

U.S. Pat. No. 4,238,294 discloses a method for recovering heavy metal ions and halogen values using anion exchange resins. The disclosed process requires that the process stream's water concentration be 20% or less by weight. The disclosed process does not incorporate any filtration process to remove particulate matter prior to ion exchange using the anion exchange resins.

Due to the enormous quantities of various aromatic carboxylic acid products now manufactured for various uses, and the high cost of catalyst materials for such processes, it is desirable to provide a cost-effective process for recovering and reusing the oxidation catalyst. The present invention provides a significant improvement over current processes by efficiently and economically recovering the expensive catalyst materials for reuse. There is also a need for a separation process which effectively separates and recovers the insoluble aromatic acid product and economically removes oxidation catalyst from the residue purge stream and recovers and recycles the catalyst to the oxidation process and at the same time allowing the undesirable impurities to remain in the residue purge stream. An additional economic benefit of this invention is the further purification of the residual aromatic acids in the purge stream which enables the manufacturer of aromatic acids to obtain some commercial value from the residual aromatic acids that are currently lost via waste disposal processes.

SUMMARY OF THE INVENTION

The present invention is an improved continuous process for the removal, recovery and recycle of oxidation catalysts and residual aromatic carboxylic acids with the undesirable impurities removed.

The present invention provides an improved separation process for the continuous catalytic oxidation of aromatic alkyls for the production of aromatic carboxylic acids in a liquid solvent medium, wherein the reactor product stream is withdrawn from the oxidation process, then separated to produce a product-containing stream, mother liquor stream and a catalyst-containing purge stream which is then passed through a filtration system and a series of sorption vessels to remove the oxidation catalyst and separate the impurities from the catalyst. The solvent is then separated from the reaction by-products by conventional distillation methods. The solvent is recycled to the process while the reaction by-product residue is disposed of either by conventional waste disposal methods, such as incineration, or may be sold into other markets. In one preferred embodiment of the invention, the oxidation catalyst is eluted from the sorption media with water; in another, a strong mineral acid is used, followed by selective precipitation of the catalyst after which the catalyst is redissolved into the reaction solvent. In the first embodiment, the recovered catalyst may then be passed through an anion ion exchange media to remove the excess bromide ion. Alternatively, after eluting the catalyst, the catalyst may be selectively precipitated as a carbonate or hydrate, followed by filtering and rinsing the precipitated catalyst which may then be redissolved in acetic acid. A selective ion exchange resin may be used for the removal of tramp metal, such as iron. The recovered oxidation catalyst is of sufficient purity that it may be directly recycled to the oxidation process.

The process of this invention is suitable for the recovery and recycle of the oxidation catalyst in the mother liquor purge stream produced from the liquid phase oxidation of aromatic alkyls to aromatic carboxylic acids. The mother liquor purge stream typically contains a lower aliphatic monocarboxylic acid, such as acetic acid, as the solvent; benzoic acid and other higher molecular weight fused ring aromatics as oxidation reaction by-products; certain undesirable aromatic carboxylic acids; cobalt, manganese, hydrobromic acid and other trace metal reaction promoters as the oxidation catalyst; and iron, chromium, and other heavy metals as process corrosion impurities.

In a first preferred embodiment, which does not involve the addition of hydrogen bromide to the process stream, the improved process comprises the steps of:

a) Maintaining the temperature of the mother liquor purge stream sufficiently high enough to keep the aromatic acids dissolved in solution, preferably from 50–100 degrees Centigrade. The required temperature will depend on the amount of aromatic acids, and reaction by-products that are present.

b) Separating the remaining insolubles by filtration at the elevated temperature. Filtration methods include but are not limited to conventional bag or cartridge filters, cross-flow membrane filtration, cross-flow microfiltration, ultrafiltration, centrifugation, and hydrocyclone separation. Hydrocyclone and centrifugation are considered less efficient at removing fines than the other separation technologies listed above.

c) Increasing the temperature of the filtered reaction solvent to maintain the solution above the saturation temperature of the soluble aromatic acids, preferably 10 degrees Centigrade above the temperature of the mother liquor purge stream.

d) Passing the solvent containing the aromatic acids, reaction by-products, corrosion products and the heavy metal oxidation catalyst though a series of cation exchange columns to remove the heavy metal ions and corrosion products.

e) Removing the heavy metal ions and corrosion products from the cation resin column by passing a solution of strong mineral acid through the columns.

f) Passing the solvent containing the aromatic acids, reaction by-products, corrosion products and oxidation catalyst through a series of anion exchange columns to remove the bromide ions.

g) Eluting the bromide ions from the anion resin column by passing a solution of sodium hydroxide through the column.

h) Passing the solvent containing the aromatic acids and reaction by-products through a column of granular activated carbon (GAC) to remove high molecular weight fused ring aromatic color formers.

i) Removing the fused ring aromatic compounds by passing a hot solution of caustic soda through the GAC.

j) Separating the aromatic acids and reactions by-products from the reaction solvent by distillation.

k) Selectively precipitating the heavy metal impurities from the oxidation catalyst by adjusting the pH of the acid solution from step (e) to 4–5, and filtering the heavy metal hydroxide solids from the acid solution. Removing residual heavy metals, such as copper, nickel and chromium by passing the filtered solution through a chelating ion exchange resin.

l) Precipitating the oxidation catalyst remaining from step (k) as the hydroxide or carbonate by adjusting the pH to 8–10 with alkaline salts, preferably sodium hydroxide or sodium carbonate.

m) Separating the precipitated catalyst from the filtrate liquor by filtration, followed by thorough rinsing of any residual dissolved salts from the filter cake.

n) Redissolving the catalyst precipitate into the recovered reaction solvent.

o) Passing the reaction solvent with the dissolved catalyst through an anion resin column (preferably a weak base type) to remove any residual chloride or sulfate ions before recycling the reaction solvent and catalyst to the oxidation process.

In a second preferred embodiment, which does involve the addition of hydrogen bromide to the process stream, the improved process comprises the steps of:

a) Maintaining the temperature of the mother liquor purge stream sufficiently high enough to keep the aromatic acids dissolved in solution, preferably 50–100 degrees Centigrade. The required temperature will depend on the amount of aromatic acids, and reaction by-products that are present.

b) Separating the remaining insolubles by filtration at the elevated temperature. Filtration methods include but are not limited to conventional bag or cartridge filters, cross-flow microfiltration, ultrafiltration, centrifugation, and hydrocyclone separation.

c) Increasing the temperature of the filtered reaction solvent to maintain the solution above the saturation temperature of the soluble acids, preferably 10 degrees Centigrade greater than the mother liquor purge stream.

d) The addition of an aqueous hydrogen bromide (HBr) solution at a sufficient concentration to form anionic metal bromide complexes with the metal oxidation catalyst ions.

e) Passing the solvent containing the aromatic acids, reaction by-products, corrosion products and the heavy metal oxidation catalyst though a series of anion exchange columns to remove the heavy metal ions and corrosion products.

f) Removing the heavy metal catalyst ions from the anion resin column by passing water through the ion exchange column which breaks down the metal bromide anionic complex into the corresponding metal cation and bromide ion.

g) Removing the residual soluble aromatic acids and reaction by-products from the reaction solvent by conventional distillation methods.

h) Removing any excess bromide ions from the recovered catalyst by passing the aqueous catalyst solution through an anionic ion exchange media that is in the "acetate" form. Alternatively, removing any excess bromide ions from the recovered catalyst by precipitating excess bromide as carbonate or hydrate.

i) Removing iron or other corrosion impurities from the recovered catalyst by passing the aqueous catalyst solution through a selective ion exchange media.

As an alternative version of these preferred embodiments of the present invention, an equivalent ion exchange process can be employed using a continuous counter current ion exchange process such as the pulse bed type known in the art as the "Higgins Loop" or a continuous countercurrent rotary bed design of the type manufactured by Advanced Separations Technology.

DETAILED DESCRIPTION OF THE PREFERRED EMBODIMENTS

Figure 1:
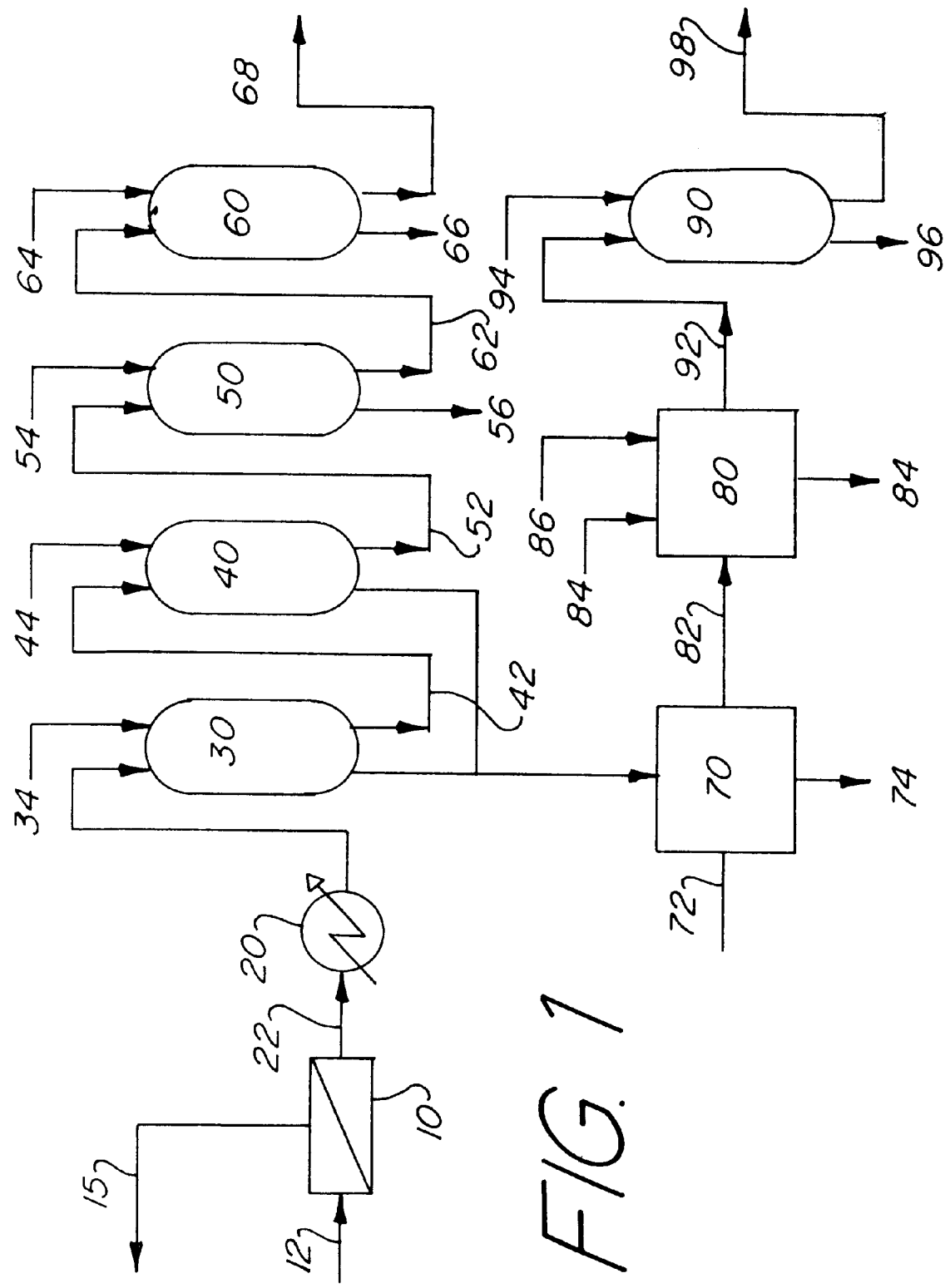
FIG. 1 is a schematic process flow diagram of the first preferred embodiment of the present invention.

In FIG. 1, a process flow diagram illustrates one embodiment of the present invention. While the present invention is susceptible to variations, the embodiment in FIG. 1 is a preferred embodiment of the invention. However, the disclosure in FIG. 1 and the detailed description of the present invention is considered an exemplification of the present invention without limitations to the specific embodiment illustrated in FIG. 1.

Referring to FIG. 1, there is shown an embodiment of a method for the recovery and recycle of the oxidation catalyst from an aromatic carboxylic acid containing manufacturing process stream utilizing the principles of the present invention.

A portion of the product containing reaction solvent stream is passed via conduit 12 to filtration system 10. System 10 removes insoluble particulate material from the reaction solvent stream. Insolubles include but are not limited to the product aromatic carboxylic acid, such as terephthalic acid (TA), since it has limited solubility in the reaction solvent. The preferred filtration system is a cross-flow membrane filtration device composed of either ceramic or sintered metal alloy materials. However, other devices are suitable provided the pore size is sufficiently small enough to remove substantially all of the particulate matter in the reaction solvent. Other devices that are suitable include bag, cartridge, or tubular filters. It is also desirable that the filtration method include means to continuously remove product aromatic acid captured on the filtering medium so as to prevent plugging the pores of the filtering medium. Cross-flow filtration is desirable for this reason. Another suitable filtration method is a filter manufactured by Funda which employs horizontal stacked plates of filtering medium and wiper arms that continuously remove captured product. While bag filters have the requisite ability to capture product fines, they also have the disadvantage of high capital cost and the tendency to load up with captured product. Cross-flow membrane filters, including ceramic filters and sintered metal filters, have the advantages of resistance to corrosion and resistance to high temperatures. The preferred operating temperature is from 35 to 100 degrees C and more preferably 50–100 degrees C.

Cross-flow filtration devices rely on recirculation of the purge stream to prevent plugging of the pores of the filtering medium. The filtering medium acts to concentrate the purge stream and allows a concentrated stream of product laden solvent to be withdrawn continuously from the filtering device. In order to prevent the plugging of the filter pores, it is desirable to maintain a high enough flow rate across the filtering medium so that turbulent flow maintains the particulate solids in suspension. It has been found that an appropriate turbulent flow is achieved if the Reynolds number for the fluid entering the cross-flow membrane filter flow channels is greater than approximately 13,000. The Reynolds Number is defined as a ratio of the dynamic forces of mass flow to the shear stress due to viscosity. It is a dimensionless number calculated as follows:

$R_e = Dv\rho/\mu$, where

D is the pipe diameter in feet, v is the fluid velocity in feet per second, $\rho$ is the fluid density in pounds per cubic foot, and $\mu$ is the absolute fluid viscosity in pounds mass per foot second.

The filtered reaction solvent stream 22 is passed through heat exchanger 20 which increases the temperature of the reaction solvent to a preferred operating temperature 10 degrees C. above the temperature of the mother liquor purge stream. The increased temperature maintains the reaction solvent above the saturation temperature of the dissolved aromatic acids.

The reaction solvent is passed via conduit 32 through ion exchange resin (IER) vessel 30. Vessel 30 removes the soluble oxidation catalyst as well as other trace metal corrosion products such as iron, nickel, and chromium. The preferred IER is a strong acid cation resin. The IER media selected can be a ResinTech CG8, Rohm & Haas IR-120, Ionac C-249, Purolite C-100 or the like. When the IER media becomes completely exhausted, that is to say, when the hydrogen ions on the IER media have been completely exchanged for the metal ions, the IER vessel is rinsed with water to remove the residual reaction solvent. The oxidation catalyst and trace metals are removed from the IER media by passing an aqueous solution of a strong acid via conduit 34 through vessel 30. The acid exchanges the metals for hydrogen ions. Strong acids suitable for the IER regeneration process include but are not limited to hydrochloric, hydrobromic and sulfuric acids. Rinse water is passed via conduit 34 to remove the residual metal containing acid and passed via conduit 36 to the catalyst purification process 70.

The reaction solvent is passed via conduit 42 through IER vessel 40. Vessel 40 serves as a "polishing" vessel. Vessel 40 removes the residual oxidation catalyst that vessel 30 does not remove. The "polishing" vessel 40 is desirable for purposes of obtaining the maximum efficiency of vessel 30 and to prevent the loss of any oxidation catalyst to the reaction solvent recovery process. The preferred IER is a strong acid cation resin. The IER media selected can be a ResinTech CG8, Rohm & Haas IR-120, Ionac C-249, Purolite C-100 or the like. When the IER media becomes completely exhausted, that is to say when the hydrogen ions on the IER media have been completely exchanged for the metal ions, the IER vessel is rinsed with water to remove the residual reaction solvent. The oxidation catalyst and trace metals are removed from the IER media by passing an aqueous solution of a strong acid via conduit 44 through vessel 40. The acid exchanges the metals for hydrogen ions. Strong acids suitable for the IER regeneration process include but are not limited to hydrochloric, hydrobromic and sulfuric acids. Rinse water is passed via conduit 44 to remove the residual metal containing acid and passed via conduit 46 to the catalyst purification process 70.

The reaction solvent is passed via conduit 52 through IER vessel 50. Vessel 50 removes free bromide ions present in the reaction solvent. The preferred IER is a weak base anion resin (gel or macroporous). The IER media selected can be a ResinTech WBMP, Rohm & Haas IR68, Ionac AFP 329, Purolite A-100, Dow WGR-2 or the like. When the IER media becomes exhausted vessel 50 is rinsed with water to remove the residual reaction solvent. The bromide ion is then removed from the IER media by passing an aqueous solution of a strong base via conduit 54 through vessel 50. The strongly basic solution exchanges the bromide ion for hydroxide ions. The strong base suitable for the regeneration process includes but is not limited to sodium or potassium hydroxide.

The reaction solvent is passed via conduit 62 through vessel 60. Vessel 60 contains granular activated carbon (GAC). The GAC adsorbs higher molecular weight fused ring aromatic color forming compounds. Removal of the color forming compounds is desirable if the residual aromatic carboxylic acids are to be recovered as a raw material for other markets. Products such as polyols, resins, and plasticizers can be manufactured from the recovered residue. A hot solution of caustic soda is passed via conduit 64 through vessel 60 to remove the fused ring aromatic compounds. The preferred temperature of the caustic soda solution is between 50 and 150 degrees C. The preferred concentration of the caustic soda solution is between 1 and 20 per cent.

The treated reaction solvent is passed via conduit 68 to the acetic acid recovery process for separating the reaction solvent from the residual aromatic acids. The reaction solvent is returned to the oxidation process. The recovered aromatic acids are of sufficient purity they can be sold as raw material into the previously mentioned markets.

The oxidation catalyst, heavy metal corrosion products and the regenerant mineral acid are passed via conduits 36 and 46 to the catalyst purification process 70. The acid solution is neutralized with a aqueous solution of a strong base to a pH of 4 to 5. Strong bases such as but not limited to sodium hydroxide or potassium hydroxide are suitable neutralizing agents. The heavy metal impurities are precipitated as a metal hydroxide sludge. The neutralized solution is passed through a filter to remove the sludge particles. Any type of filter device is suitable provided the pore size is small enough to remove the particulate heavy metal sludge. Suitable devices are bag, cartridge, plate/frame and tubular cross-flow filters. The filtered oxidation catalyst solution may be passed through a chelating ion exchange resin to remove residual heavy metals, such as copper, nickel and chromium. Suitable clelating ion exchange resins include polystyrene resins with amino-diacetic acid functionality, such as Sybron SR-5, Rohm & Haas IR718 or Resintech SIR300. The filtered oxidation catalyst solution is passed via conduit 82 to the oxidation catalyst conversion process 80.

The oxidation catalyst consisting of cobalt and manganese is precipitated as a hydrate, carbonate or bicarbonate by the addition via conduit 84 of a soluble carbonate, bicarbonate or hydroxide compound. Any number of compounds are suitable for providing the required anion for precipitating the metal catalyst such as sodium carbonate, sodium bicarbonate, or sodium hydroxide. The pH of the solution should be adjusted to 8.5 to 9.5. The Co/Mn slurry is filtered through a filtration device, preferably a plate and frame filter press which separates the Co/Mn solids from the salt solution. Other suitable filtration devices include a horizontal plate filter such as the type manufactured by Funda or the sintered metal tubular filter manufactured by Mott Metallurgical. The filter cake is thoroughly rinsed with demineralized water to remove the soluble salts. The Co/Mn catalyst is dissolved into the recovered reaction solvent (acetic acid) by passing the reaction solvent via conduit 86 through the filter until the filter cake is completely dissolved. The filtrate is passed via conduit 88 to waste treatment. The filtrate contains typically the sodium or potassium salt of the mineral acid; e.g., sodium chloride or potassium sulphate.

The cobalt/manganese acetate solution is passed via conduit 92 through IER vessel 90. Vessel 90 contains a weak base anion IER media which removes any trace amounts of mineral acid anions such as but not limited to chlorides or sulfates. The cobalt/manganese acetate solution is returned via conduit 98 to the oxidation process.

The IER media is regenerated with an aqueous solution of a strong base via conduit 94 to remove the mineral anion. The strong base suitable for regenerating the IER media includes but is not limited to sodium hydroxide. The sodium salt created from the regeneration of the IER media is passed via conduit 96 to waste treatment.

An example of the performance of the previously described catalyst recovery process and illustrated in FIG. 1 is shown in the following table:

TABLE I

Removal of Catalyst from a Synthetic Reaction Solvent Utilizing an Ion Exchange Resin

| Components | Feed | IER Effluent |
| --- | --- | --- |
| Acetic Acid, % | 95 | 95 |
| Water, % | 5 | 5 |
| Cobalt, PPM | 1,100 | <1 |
| Manganese, PPM | 200 | <1 |
| Feed Rate, ml/min | 20 | |
| Temperature, C. | 49 | 49 |
| Resin Type | Sulfonated Polystyrene | — |
| Resin Vol, ml | 400 | — |
| Acetic A. Vol, ml | 12,400 | — |

The data in Table I clearly demonstrates the efficient removal of the cobalt/manganese catalyst utilizing a laboratory prepared sample.

Figure 2:
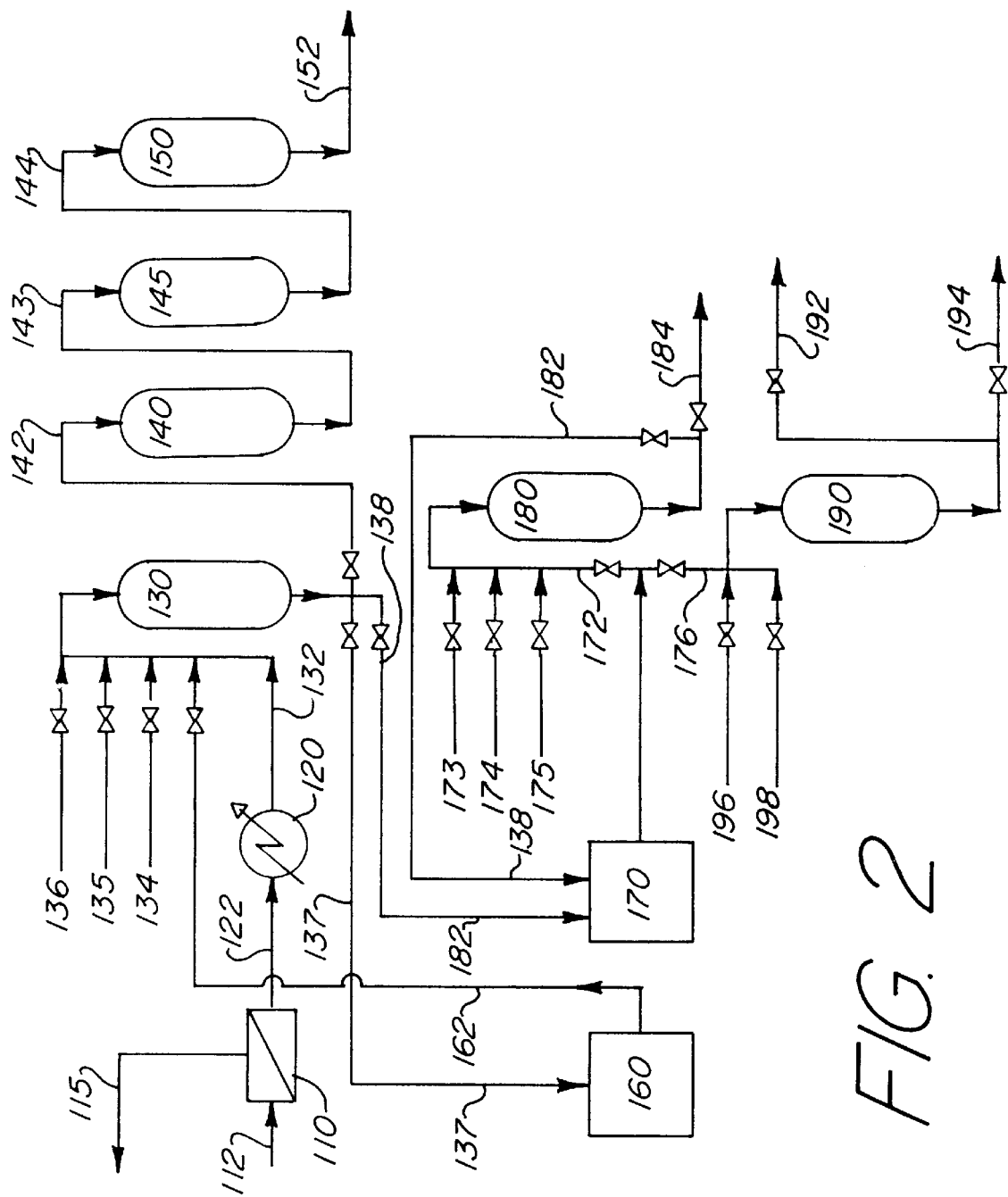
FIG. 2 is a schematic process flow diagram of the second preferred embodiment of the present invention.

Referring to FIG. 2, there is shown a second embodiment of a method for the recovery and recycle of the oxidation catalyst from an aromatic carboxylic acid containing manufacturing process stream utilizing the principles of the present invention.

The acetic acid purge stream containing the oxidation catalyst is passed via pipe 112 to filtration system 110. System 110 removes insoluble aromatic aids from the reaction solvent stream. The major constituent in the insolubles include the aromatic carboxylic acid product since it has limited solubility in the reaction solvent. The retentate stream 115 returns the aromatic acid product to the purge feed tank. A bleed stream from the purge feed tank is returned to the aromatic acid manufacturing process. The preferred filtration system is a cross-flow filtration device. The preferred material of construction of the cross-flow filter is ceramic or sintered powder metal alloys. However, other filtration devices are suitable provided the pore size is sufficiently small enough to remove substantially all particulate matter in the reaction solvent. The removal of particulate matter by filtration is the preferred method, other methods are suitable, however are not as efficient. One example is upflow through the sorption media which allows the particulate matter to pass through. Other filtration devices that are suitable include bag, cartridge, tubular filters, and centrifugal devices. The preferred operation temperature is from 35 C. to 120 C. and more preferably from 50–100 degrees C.

The acetic acid purge stream 122 is passed through heat exchanger 120 which increases the temperature of the reaction solvent to a higher preferred operating temperature of 10 degrees C. above the feed stream. The increased temperature maintains the liquid above the saturation temperature of the dissolved aromatic acids.

An aqueous solution of hydrobromic acid (HBr) is injected via line 135 into acetic acid purge stream 132 at a sufficient stoichiometric ratio to form the respective cobalt and manganese anionic bromide complexes. The sorption media can consist of any one of several anion ion exchange resins. The anion ion exchange media can be either a strong or weak base type. The ion exchange media selected can be the strong base type such as, but not limited to Sybron ASB1 or a weak base type such as but not limited to Rohm and Haas IRA67. The preferred anion ion exchange media is a pyridine based anion ion exchange resin such as but not limited to a Reillex HP or HPQ. Other ion exchange media based on pyridine chemistry are also acceptable. The anion sorption media is converted into the bromide form by passing a solution containing bromide ion through the media. The preferred solution is hydrobromic acid (HBr) since it is typically part of the oxidation system.

The acetic acid purge stream 132 is passed through sorption vessel 130 which contains the anion sorption media. Vessel 130 removes the oxidation catalyst as an anionic metal bromide complex. The acetic acid effluent from vessel 130 passes via line 142 through polishing vessel 140 which also contains the anion sorption media. Sorption in vessel 130 is exhausted to the extent that the catalyst concentration in the effluent is at least 50% of the catalyst concentration in the acetic acid purge feed. The use of polishing vessel 140 allows for maximum utilization of the sorption media in vessel 130 and protection of loss of the oxidation catalyst.

The effluent of vessel 140 is passed via line 143 to vessel 145. Vessel 145 removes free bromide ions present in the effluent. The preferred IER is a weak base anion resin (gel or macroporous). The IER media selected can be a Resin-Tech WBMP, Rohm & Haas IR68, Ionac AFP 329, Purolite A-100, Dow WGR-2 or the like. When the IER media becomes exhausted vessel 145 is rinsed with water to remove the residual reaction solvent. The bromide ion is then removed from the IER media by passing an aqueous solution of a strong base through vessel 145. The strongly basic solution exchanges the bromide ion for hydroxide ions. The strong base suitable for the regeneration process includes but is not limited to sodium or potassium hydroxide.

The effluent of vessel 145 is passed via line 144 to an acetic acid recovery process which separates the acetic acid from the residual aromatic acids. The purified acetic acid is then returned to the oxidation process.

An optional step in the catalyst recovery process is to pass the effluent of vessel 145 via line 144 through vessel 150 which contains granular activated carbon (GAC). The GAC removes higher molecular weight fused ring aromatics which are color formers. The effluent of the GAC vessel is passed via line 152 to the acetic acid recovery process. The recovered acetic acid is returned to the oxidation process. The performance of this treatment process is illustrated in example 4. The purified residual aromatic acids have economic value as raw material for polyester polyols and unsaturated polyester resins. The GAC can be regenerated by rinsing the GAC media with water followed by hot (70–90 degrees C.) caustic soda solution (5–10%). The higher weight aromatics are removed from the GAC as the soluble sodium salt and disposed of in conventional biological waste treatment systems.

The oxidation catalyst is eluted from vessel 130 by passing water via line 136 through the sorption media. The anionic metal complexes of cobalt and manganese break down in the presence of water to form their corresponding metal cation and bromide anion. A concentrated catalyst solution (4–5% metals) is obtained by the controlled elution with water and is passed via 138 to vessel 170. During the final elution step the water contains relatively low concentrations of cobalt and manganese (<5,000 ppm). This "tails" solution is passed via line 137 to vessel 160 and is recycled via line 162 for the next catalyst elution. Maximum oxidation catalyst recovery efficiencies of greater than 98% can be obtained by recycling the elution "tails".

If the recovered catalyst has too much water, optionally, conventional reverse osmosis technology may be used to permeate excess water from the catalyst.

The recovered oxidation catalyst contains an excess amount of bromide ion versus the typical metal-to-bromide ratios required for the oxidation process. This excess bromide ion in the recovered catalyst is removed by passing the catalyst solution via line 172 through vessel 180 which contains a anion exchange resin such as but not limited to IRA67, Purolite 845 or Sybron ASB1. The anion resin can be either a weak or strong base, however the preferred anion resin is a weak base type. The anion IER is in the acetate form which results in the exchange of an equivalent of acetate ion for an equivalent of bromide ion. The effluent of the bromide removal vessel 180 is recirculated to vessel 170 via line 182. When the correct ratio of metal to bromide is obtained the recirculation is stopped and the residual catalyst solution in vessel 180 is purged to vessel 170 with acetic acid.

Rather than employing an ion exchange process, alternatively, the excess bromide ion could be removed by selectively precipitating the bromide as a carbonate or hydrate. The precipitated bromide is then filtered, rinsed and redissolved in acetic acid.

The residual acetic acid is purged to the recovered catalyst vessel 170 with demineralized water. The ion exchange media is then regenerated with an aqueous caustic soda solution, using conventional ion exchange regeneration procedures. The anion resin is then converted to the acetate form by passing an aqueous acetic acid solution through vessel 170. The ion exchange media is then ready for the next bromide removal cycle.

The catalyst sorption process provides efficient recovery of cobalt and manganese while allowing metal corrosion impurities such as nickel and chromium to pass through to the acetic acid recovery process. However, iron as a corrosion impurity, can accumulate in the recovered catalyst solution and is removed by passing the recovered catalyst solution from vessel 170 via line 176 through vessel 190. Vessel 190 contains a selective ion exchange media that removes iron in the presence of cobalt and manganese. The selective ion exchange media may be such as but not limited to Resintech SIR-500, Rohm & Haas IR-718, Purolite S-950, or Eichrome Diphonix. The preferred selective resin is a strong acid cation resin containing diphosphoric acid functional groups manufactured by Eichrome Industries. The recovered catalyst is passed via line 176 through vessel 190 which selectively removes the iron. The purified oxidation catalyst is then returned to the oxidation process via line 192.

The selective IER in vessel 190 is regenerated by passing a solution of concentrated mineral acid via line 196 through vessel 190. Mineral acids such as but not limited to hydrochloric, hydrobromic, and sulfuric acid. The preferred acid is hydrochloric acid. The iron chloride solution can be precipitated by neutralization with an alkali chemical such as lime or caustic soda. The iron sludge is then disposed of in the appropriate manner. An alternative regeneration method is to rinse vessel 190 with a dilute aqueous solution of hydrobromic acid which will remove any residual cobalt that may also be chemically exchanged on to the selective resin. A concentrated solution of HBr, preferably 25–48% HBr, can be passed through the selective resin in vessel 190. The iron removed from the selective resin converts into an anionic bromide complex in the presence of concentrated HBr. The iron bromide anionic complex can be removed by passing the solution through a anion IER in the bromide form. The iron bromide is removed by water elution and the concentrated HBr is reused for the next regeneration of vessel 190. The iron can then be disposed of by conventional precipitation methods. The recovered cobalt can be recycled to the recovered catalyst storage tank. The IER media in vessel 190 is thoroughly rinsed with deionized water after regeneration.

The performance of the previously described oxidation catalyst recovery process and illustrated in FIG. 1 is shown in the following examples:

Example 1

| Resin Type: | Strong Base Anion | | |
|---|---|---|---|
| Resin Manufacturer: | Sybron Chemicals | | |
| Resin Designation: | ASB1 | | |
| Description: | Crosslinked polystyrene with quaternary amine functionality | | |
| Resin Bed Volume: | 100 ml | | |
| Flow Rate: | 4 BV/Hr | | |
| Temperature: | amb. | | |
| Analysis - ppm by wt | Feed | Effluent | Eluted Catalyst |
| Co | 486 | 0 | 10,500 |
| Mn | 485 | 3.7 | 5,970 |
| Fe | 2 | 0 | 14 |
| Ni | 3 | 0 | 13 |
| Cr | 7 | 3.9 | 12.5 |
| Br | 3,200 | | 17,250 |

Example 2

| Resin Type: | Weak Base Anion | | |
|---|---|---|---|
| Resin Manufacturer: | Rohm and Haas Company | | |
| Resin Designation: | IRA 67 | | |
| Description: | Crosslinked acrylic resin with tertiary amine functionality | | |
| Resin Bed Volume: | 100 ml | | |
| Flow Rate: | 4 BV/Hr | | |
| Temperature: | Amb. | | |
| Analysis - ppm by wt | Feed | Effluent | Eluted Catalyst |
| Co | 486 | 1.5 | 5,120 |
| Mn | 485 | 9.1 | 2,070 |
| Fe | 2 | 3.4 | 37 |
| Ni | 3 | .6 | 4 |
| Cr | 7 | 5.05 | 5 |
| Br | 3,200 | | 25,500 |

Example 3

| Resin Type: | Intermediate Strong/Weak Base Anion | | |
|---|---|---|---|
| Resin Manufacturer: | Reilly Industries | | |
| Resin Designation: | HPO | | |
| Description: | Crosslinked polyvinylpyridine with Methyl Chloride Quaternary functionality | | |
| Resin Bed Volume: | 100 ml | | |
| Flow Rate: | 4 BV/Hr | | |
| Temperature: | amb. | | |
| Analysis - ppm by wt | Feed | Effluent | Eluted Catalyst |
| Co | 486 | 0 | 57,900 |
| Mn | 485 | 0 | 28,300 |
| Fe | 2 | 0 | 102 |
| Ni | 3 | 0 | 91 |
| Cr | 7 | 2.7 | 107 |
| Br | 3,200 | | 30,850 |

The foregoing examples demonstrate that the efficient removal and recovery of the oxidation catalyst can be readily achieved by the present invention. What has been illustrated and described herein is a method for recovering the oxidation catalyst from the acetic acid purge stream and then removing corrosion metal impurities from the catalyst, and removing the excess bromide ion. The recovered oxidation catalyst meets or exceeds process specifications for manufactured oxidation catalyst.

Excess water in the mother liquor purge stream may interfere with the efficiency of the ion exchange resins. Preferably the water content is less than approximately 20%. This problem can be overcome by recycling recovered solvent to the mother liquor purge stream so as to maintain the water content of the mother liquor purge stream at approximately 20% or less.

The present invention has been illustrated and described with reference to specific embodiments, the present invention is not limited thereto. These are alternative modifications which will become apparent to those skilled in the art upon reading the foregoing description. Accordingly, such alternatives, changes and modifications, are to be considered as forming a part of the present invention is so far as they fall within the intent and scope of the claims described.

I claim:

1. A process for the recovery and recycle of the oxidation catalyst and product aromatic carboxylic acid in the mother liquor purge stream purged from the mother liquor after separation of the product aromatic carboxylic acid produced from the liquid phase oxidation of aromatic alkyls to aromatic carboxylic acids in which the mother liquor purge stream contains a lower aliphatic monocarboxylic acid as solvent; reaction by-products; aromatic carboxylic acid fines; oxidation catalyst comprising cobalt, manganese, and hydrobromic acid; and process corrosion byproducts, comprising the steps of:

(a) filtering the mother liquor purge stream through a filter medium to recover and recycle insoluble aromatic carboxylic acid fines and other insolubles;

(b) passing the solvent containing the, reaction by-products, corrosion byproducts and the oxidation catalyst through a series of ion exchange columns to remove the oxidation catalyst and corrosion byproducts; and (c) eluting the oxidation catalyst and corrosion byproducts from the ion exchange columns.

2. The process of claim 1 wherein the filtration of step (a) further comprises the step of continuously recovering and recycling captured insoluble aromatic carboxylic acid lines and other insolubles from the filter media.

3. The process of claim 2 wherein the filtration of step (a) is by an ultrafiltration filter medium.

4. The process of claim 2 wherein the filtration of step (a) is by a microfiltration filter medium.

5. The process of claim 2 wherein the filtration of step (a) is by a membrane filter medium.

6. The process of claim 2 wherein the filtration of step (a) is by a cross-flow filter medium.

7. The process of claim 2 wherein the filtration of step (a) is by a hydrocyclone filter medium.

8. The process of claim 6 wherein the filtration of step (a) is by a cross-flow ceramic microfiltration filter medium.

9. The process of claim 2 wherein the filtration of step (a) is by a bag filter medium.

10. The process of claim 2 wherein the filtration of step (a) is by stacked filter plates incorporating a wiper bar for the continuous removal of insoluble aromatic carboxylic acid lines and other insolubles captured on the stacked filter plates.

11. The process of claim 6 wherein the filtration of step (a) is by a sintered metal cross-flow microfiltration filter medium.

12. The process of claim 8 wherein the filtration of step (a) comprises recirculating the mother liquor purge stream across the cross-flow microfiltration filter medium to prevent the plugging of the cross-flow microfiltration filter medium.

13. The process of claim 12 wherein the recirculating of the mother liquor purge stream is maintained at a flow rate sufficient to maintain a Reynolds number of at least approximately 13,000.

14. The process of claim 1 further comprising the steps of maintaining the temperature of the mother liquor purge stream sufficiently high enough to keep the aromatic acid lines dissolved in solution; and carrying out the filtration of step (a) at the elevated temperature.

15. The process of claim 14 further comprising the step of increasing the temperature of the filtered reaction solvent to maintain the solution above the saturation temperature of the soluble aromatic acids prior to step (b).

16. The process of claim 15 further comprising carrying out the elution of step (c) by passing a solution of strong mineral acid through the columns.

17. The process of claim 16 further comprising passing the solvent containing the aromatic acids, reaction by-products, corrosion byproducts and oxidation catalyst through a series of anion exchange columns to remove excess bromide ions.

18. The process of claim 17 further comprising eluting the bromide ions from the anion exchange columns by passing a solution of sodium hydroxide through the columns.

19. The process of claim 18 further comprising passing the solvent containing the aromatic acids and reaction by-products through a column of granular activated carbon (GAC) to remove high molecular weight fused ring aromatic color formers.

20. The process of claim 18 further comprising removing the fused ring aromatic compounds from the GAC by passing a hot solution of caustic soda through the GAC.

21. The process of claim 20 further comprising separating the aromatic acids and reactions by-products from the reaction solvent by distillation.

22. The process of claim 21 further comprising selectively precipitating the process corrosion byproducts from the oxidation catalyst as hydroxide solids by adjusting the pH of the acid solution to 4–5, and filtering the hydroxide solids from the acid solution.

23. The process of claim 22 further comprising the additional step of passing the filtered acid solution through a chelating resin to remove residual process corrosion byproducts from the filtered acid solution.

24. The process of claim 23 further comprising precipitating the oxidation catalyst remaining as the hydroxide or carbonate by adjusting the pH to 8–10 with alkaline salt and separating the precipitated catalyst from the filtrate liquor by filtration, followed by rinsing of any residual dissolved salts from the filter cake.

25. The process of claim 24 further comprising redissolving the catalyst precipitate into the recovered reaction solvent; and passing the reaction solvent with the dissolved catalyst through an anion resin column to remove any residual chloride or sulfate ions before recycling the reaction solvent and catalyst to the oxidation process.

26. The process of claim 25 wherein the filtration of step (a) is by bag filters.

27. The process of claim 25 wherein the filtration of step (a) is by cartridge filters.

28. The process of claim 25 wherein the filtration of step (a) is by cross-flow microfiltration.

29. The process of claim 25 wherein the filtration of step (a) is by ultrafiltration.

30. The process of claim 25 wherein the alkaline salt is sodium hydroxide.

31. The process of claim 25 wherein the alkaline salt is sodium carbonate.

32. The process of claim 25 wherein the anion resin column is a weak base type.

33. The process of claim 25 wherein the ion exchange columns of step (b) are of the continuous counter current type of ion exchange process.

34. The process of claim 25 wherein the continuous counter current type of ion exchange process is a pulse bed type.

35. The process of claim 25 wherein the continuous counter current type of ion exchange process is a continuous countercurrent rotary bed type.

36. The process of claim 16 further comprising the steps of adding an aqueous hydrogen bromide (HBr) solution at a sufficient concentration to form anionic metal bromide complexes with the metal oxidation catalyst ions.

37. The process of claim 36 further comprising carrying out the elution of step (c) by passing water through the ion exchange column which breaks down the metal bromide anionic complex into the corresponding metal cation and bromide ion.

38. The process of claim 37 further comprising removing the residual soluble aromatic acids and reaction by-products from the reaction solvent by conventional distillation methods.

39. The process of claim 38 further comprising removing any excess bromide ions from the recovered catalyst by passing the aqueous catalyst solution through an anionic ion exchange media that is in the "acetate" form.

40. The process of claim 39 wherein the filtration of step (a) is by bag filters.

41. The process of claim 39 wherein the filtration of step (a) is by cartridge filters.

42. The process of claim 39 wherein the filtration of step (a) is by cross-flow microfiltration.

43. The process of claim 39 wherein the filtration of step (a) is by ultrafiltration.

44. The process of claim 39 further comprising the step of removing process corrosion byproducts from the recovered catalyst by passing the aqueous catalyst solution through a selective ion exchange media.

45. The process of claim 39 further comprising the step of recycling the elution tails.

46. The process of claim 39 wherein the ion exchange columns of step (b) are of the pyridine type.

47. The process of claim 1 wherein the recovered oxidation catalyst contains excess bromide ion, further comprising the step of passing the recovered oxidation catalyst through an anion ion exchange resin to remove excess bromide ion.

48. The process of claim 1 further comprising the step of recycling recovered solvent to the mother liquor purge stream to dilute excess water in the mother liquor purge stream.

49. The process of claim 48 wherein the water content in the mother liquor purge stream is maintained at 20% or less.

50. The process of claim 1 wherein the ion exchange columns of step (b) are strong base anion resins comprising cross linked polystyrene with quarternary amine functionality.

51. The process of claim 1 wherein the ion exchange columns of step (b) are weak base anion resins comprising cross linked polystyrene with tertiary amine functionality.

52. The process of claim 1 wherein the ion exchange columns of step (b) are weak base anion resins comprising cross linked acrylic resin with tertiary amine functionality.

53. The process of claim 1 wherein the ion exchange columns of step (b) are strong acid cation resins comprising sulfonated polystyrene.

54. The process of claim 1 wherein the ion exchange columns of step (b) are intermediate strong/weak base anion resins comprising cross linked polyvinyl pyridine with methyl chloride quarternary functionality.

55. The process of claim 1 wherein the recovered oxidation catalyst contains excess water, further comprising the step of permeating excess water from the recovered oxidation catalyst by reverse osmosis.

* * * * *